United States Patent [19]

Kakimoto

[11] Patent Number: 5,525,097
[45] Date of Patent: Jun. 11, 1996

[54] AIR MOTOR

[75] Inventor: Masakazu Kakimoto, Aichi-ken, Japan

[73] Assignee: UHT Corporation, Aichi-Ken, Japan

[21] Appl. No.: 357,652

[22] Filed: Dec. 16, 1994

[30] Foreign Application Priority Data

Aug. 9, 1994 [JP] Japan .................... 6-187102

[51] Int. Cl.⁶ .................... B24B 5/00; F03B 13/04
[52] U.S. Cl. .................... 451/295; 415/200; 415/904; 418/270
[58] Field of Search .................... 451/295, 294; 173/218, 219, 205; 418/270; 415/200, 202, 904

[56] References Cited

U.S. PATENT DOCUMENTS

| | | | |
|---|---|---|---|
| 2,251,057 | 7/1941 | Iseman | 451/295 |
| 2,545,453 | 3/1951 | Forss | 451/295 |
| 2,724,573 | 11/1955 | Lundquist | 173/205 |
| 3,827,834 | 8/1974 | Kakumoto | 418/270 |
| 4,040,311 | 8/1977 | Page, Jr. et al. | 415/503 |
| 4,167,062 | 9/1979 | Page, Jr. et al. | 415/503 |
| 5,074,750 | 12/1991 | Kakimoto | 415/200 |
| 5,211,531 | 5/1993 | Kakimoto | 415/112 |
| 5,309,714 | 5/1994 | Putney et al. | 173/219 |

*Primary Examiner*—Bruce M. Kisliuk
*Assistant Examiner*—Dona C. Edwards
*Attorney, Agent, or Firm*—Greenblum & Bernstein

[57] ABSTRACT

Disclosed is an air motor having an engine pack (with a rotor provided with front and rear retainers, a stator, and vanes) which can be assembled and replaced even by an unskilled person. An air supply joint is engaged with guide projections formed on the inner peripheral surface of a housing, with its forward end portion held in contact with the rear retainer; the forward end portion being fastened by a nut member which is threadedly engaged with the housing. On the rear face of the forward end portion are formed a plurality of first projections produced of a rigid synthetic resin, and on the front face of the nut member corresponding to the first projection are formed a plurality of second projections, so that a firm relation of engagement is established by an elastic force of restoration of the first projection; that is, the nut member will not accidentally become loose owing to the locking effect of the first and second projections. Furthermore, the engine pack can be drawn out straight by unfastening the nut member by a jig.

6 Claims, 7 Drawing Sheets

AIR MOTOR

BACKGROUND OF THE INVENTION

The present invention relates to an air motor to be used as a driving power source of industrial machines and equipment such as an air grinder for grinding and polishing operation or handpieces for odontotherapy.

Figure 12:
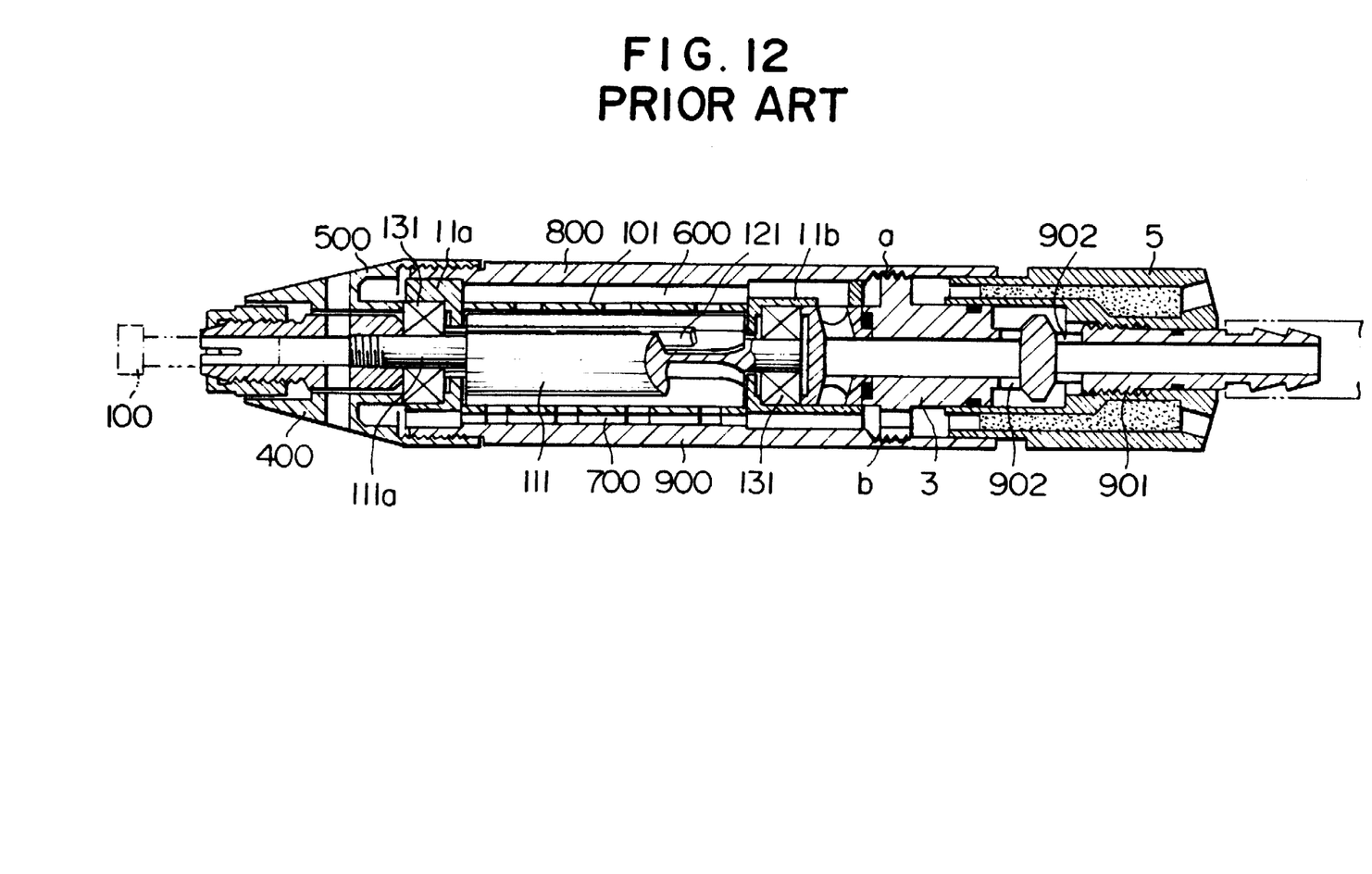
FIG. 12 is a longitudinal sectional view of a prior art example.

An air motor to be used as a driving power source not only for grinding and polishing operation but for handpieces and so forth for odontotherapy is generally of the construction as shown in FIG. 12.

Briefly, the air pack comprises a grinding-polishing tool unit which rotatably supports a desired grinding-polishing tool 100 and is enclosed in a casing 500; a power unit 900 including a front retainer 11a, a rear retainer 11b, a rotor 111 rotatably supported by the front and rear retainers 11a and 11b and having a plurality of vanes 121 which can be moved in and out, a stator 101 holding the rotor 111 located between the front retainer 11a and the rear retainer 11b, and an air supply passage 600 and an air discharge passage 700, which are all enclosed in a casing 800; and an air supply joint 3 for adjusting the amount of compressed air to be supplied to the power unit 900. The grinding-polishing tool unit 400 is threadedly connected to the power unit 900, and the air supply joint 3 is formed of a valve body 901 having an air supply hole 902 through which the air is supplied to the power unit 900, and a grip portion 5 movably engaged by a screw with the valve body 90 for adjusting the amount of opening of the air supply hole 902.

In the case of the above-described prior art, the forward end of the valve body 901 is threadedly engaged with the inner peripheral surface of the casing 900 of the power unit 900 into contact with the retainer 11b, and further the engaged portion a is fixedly secured with adhesive; therefore when disengagement of this engaged portion a is required, the adhesive b must be removed after softening the adhesive b by heating up to around 100° C. The above-described operation, however, is very inconvenient because it requires a special technique for replacement of the power unit 900 without deteriorating durability thereof.

Furthermore, the internal pressure of the power unit 900 (the internal pressure of the stator 101) becomes very high during operation and leaks out, though little despite of an airtight design, to thereby force a lubricant such as grease out from a bearing section 131 of a rotor shaft 111a, resulting in oil starvation and accordingly seriously deteriorated durability due to a failure in withstanding high-speed operation. In addition, because of the construction that vibration of the power unit 900 passes directly to a user's hand and fingers, the user will be likely to feel fatigued.

Furthermore, the grip section 5 opens the valve when turned counterclockwise and closes the valve when turned clockwise. However, if the counterclockwise turn of the grip section 5 is carelessly kept on, the grip section 5 will in some case drop from the air supply joint 3. Therefore the air motor is not necessarily convenient for the use lacking in a special knowledge concerned.

SUMMARY OF THE INVENTION

In view of the above-described various problems in the heretofore known art, it is an object of the present invention to provide an air motor which enables even an unskilled person not only to assemble the air motor but to replace an engine pack (including front and rear retainers, a stator, and a rotor having vanes).

It is another object of the present invention to provide an air motor which assures prolonged service life and very good feel of use.

According to a technological means adopted for the accomplishment of the aforesaid objects, first aspect of the present invention presents the following essential point that a cartridge-type engine pack is composed of an air supply passage and an air discharge passage formed of longitudinal grooves in the inner peripheral surface of a pipe-like case which closes a front open section and a rear open section respectively with a front retainer and a rear retainer each having a bearing section, a stator with an air supply port communicating with the air supply passage and an air discharge port communicating with the air discharge passage between the front and rear retainers to open each of a communicating air supply passage and a communicating air discharge passage which communicate with the air supply passage and the air discharge passage respectively, and a rotor having a plurality of vanes and rotatably supported within the stator by the bearing section of the front and rear retainers, the air motor comprises, beside the engine pack, a grinding-polishing tool unit straightly releasably connecting a rotating shaft to a rotor shaft projecting from the engine pack, a straightly removable air supply joint communicating with the communicating air supply passage of the rear retainer, and a housing which contains the grinding-polishing tool and the engine pack longitudinally releasably inserted in order of mention in a fitted state from a rear opening and is opened at both ends in order to allow projection of the grinding-polishing tool out through the front opening; the air supply joint having a forward end portion which slides into unrotatable engagement with guide projections projectively formed on the inner peripheral surface of the housing in such a manner that it will contact the rear retainer, thereby communicating with the communicating air supply passage, An air supply tube section connected with the forward end portion; and a plurality of first projections produced of a rigid synthetic resin, projecting at an appropriate spacing on the same circumference of the rear surface of the forward end portion; a nut member having a clearance hole into which the air supply tube section is inserted, and movably engaged by screw threads with the inner peripheral surface of the housing; and a plurality of second projections projectively formed at an appropriate spacing for elastically pressing the first projections against the same circumference of the front surface of the nut member.

The essential point of second aspect of the present invention resides in that the housing of the first aspect is separable into a half body of housing formed integrally with the grinding-polishing tool unit and a housing body for the engine pack; the half body of housing being removably engaged with the housing body.

The essential point of third aspect of the present invention is that the engine pack of the first aspect has a slight clearance communicating with the exterior between the outer peripheral surface thereof and the inner peripheral surface of the housing. The essential point of fourth aspect of the present invention lies in that the engine pack of the first aspect is provided with an elastic circular member mounted, in an optional place on the outer peripheral surface thereof, in tight contact with the inner peripheral surface of the housing, for absorbing vibration.

The essential point of fifth aspect of the present invention is that the front retainer of the first aspect has a discharge passage for discharging a part of air to be discharged and an escape groove for allowing the inside air to the engagement section of the front retainer with the bearing section; the discharge passage and the escape groove being connected with several air discharge grooves formed in the inner peripheral surface of the housing section of the grinding-polishing tool unit; and the air discharge groove being open to the outlet where the grinding-polishing tool protrudes.

Furthermore, sixth aspect of the present invention has the essential point that the air supply joint of the first aspect has an air supply port communicating with a compressed air supply source, a grip section which is threadedly engaged with the air supply joint, for closing the air supply port when moved forward and for adjusting the amount of opening of the air supply port when moved backward, and a split ring removably mounted on the base end side of the air supply joint for preventing backward movement of the grip over a specific position.

According to the above-described technological means, the air motor of the present invention has the following function.

1. From one open section, that is, the rear open section, of the housing, the grinding-polishing tool unit and the engine pack are inserted in the written order until the rotor shaft of the engine pack is straightly engaged with the rotating shaft of the grinding-polishing tool unit; and then the air supply joint is mounted to communicate with the communicating air supply passage of the rear retainer of the engine pack. The installation of the air supply joint to the engine pack is by the following procedure: the forward end portion is first engaged with the guide projections projectively provided on the inner peripheral surface of the housing, into contact with the rear retainer, and then is tightened by a nut member threadedly mounted in the housing. In this case, since A plurality of first projections produced of a rigid synthetic resin are mounted at an appropriate spacing on the rear surface of the forward end portion, and a plurality of second projections are also projectively provided on the front surface of the nut member correspondingly to the first projections, the elastic force for restoration of the first pusher produces a firm relation of engagement when the nut member is tightened; and therefore the forward end portion will never become loosened due to the locking effect of the first and second projections.

The compressed air advances through the communicating air supply passage of the rear retainer in the air supply joint, the air supply passage in the pipe-like case, and the air supply port of the stator, thus being injected to the vanes to drive the rotor at a high speed and accordingly to turn a desired grinding-polishing tool mounted on the forward end of the grinding-polishing tool unit.

In the meantime, when the engine pack is to be removed, the nut member is unfastened by turning with a jig, and after the removal of the air supply joint, the engine pack is drawn straightly out to disconnect the rotating shaft of the grinding-polishing tool unit from the rotor shaft.

2. In the grinding-polishing tool unit the housing is separate from the housing body containing the engine pack. Therefore, even an angle-type grinding-polishing tool unit which can not be installed to a straight tube-type housing can be installed and disassembled.

3. The slight clearance provided between the outer peripheral surface of the engine pack and the inner peripheral surface of the housing serves to let out the air compressed at the time of setting to the housing.

4. Vibration during rotation is absorbed by the elastic annular member mounted on the outer peripheral surface of the engine pack and therefore will not be transmitted to the housing.

5. The air discharge passage provided in the front retainer and the escape groove formed between the front retainer and the bearing section communicate with the opening into which the grinding-polishing tool protrudes out, through the air discharge groove formed in the inner peripheral surface of the housing of the grinding-polishing tool unit. Therefore, the bearing section of the grinding-polishing tool unit is effectively cooled down during operation, thereby preventing splash of a lubricant such a grease likely to be caused by a high pressure in the stator.

6. At a specific valve opening, the rear end of the grip portion hits against the split ring mounted on the base end of the air supply joint, preventing further backward movement of the grip portion.

The air motor of the above-described constitution according to the present invention has the following advantages.

1. The present invention presents a simple method including engaging the forward end portion of the air supply joint with the guide projections projectively provided on the inner peripheral surface of the housing until it contacts the rear retainer, and tightening the forward end portion thus threadedly engaged with the housing, by the nut member which moves back and forth; however, the forward end portion will never loosen owing to the locking effect of the first projections produced of a rigid synthetic resin on the rear surface of the forward end portion and the second projections of the nut member; and moreover because the first and second projections are firmly held engaged with the elastic force of restoration of the first projections, the air supply joint for supplying the compressed air to the engine pack in the housing can be firmly connected through screw threads without using an adhesive, simply by fastening the nut member after inserting the engine pack straight into the housing so that the rotor shaft will engage with the rotating shaft of the grinding-polishing tool unit inserted in the housing, and further can be removed from the engine pack simply by removing the nut member.

Therefore, even an unskilled person is able to not only easily assemble the air motor by connecting the grinding-polishing tool unit, the engine pack and the air supply joint with one another but also disassemble the air motor for replacement of the engine pack or other when required.

2. Even such an air motor having an angle-type grinding-polishing tool unit can easily be assembled and disassembled for replacement of the grinding-polishing tool unit, the engine pack and the air supply joint.

3. Since a very small clearance is established to communicate with the outside between the outer peripheral surface of the engine pack and the inner peripheral surface of the housing, to thereby let out the air compressed at the time of insertion of the engine pack into the housing, it is possible to set the engine pack exactly in engagement with the grinding-polishing tool unit.

4. An elastic annular member is mounted on the outer peripheral surface of the engine pack to absorb vibration occurring during tool rotation, thereby improving the feeling of grip of the housing; therefore a user can handle the tool quite easily without getting tired with vibration even after a long-time use.

5. A part of the air to be discharged and leakage air from the stator are discharged at the opening for projection of the grinding-polishing tool, through the discharge passage in the front retainer, the escape groove formed in the engaging portion between the front retainer and the bearing section, and several air discharge grooves formed in the inner peripheral surface of the housing section of the grinding-polishing tool unit; therefore, the bearing section of the grinding-polishing tool unit which is liable to get overheated during high-speed operation can be cooled effectively and in addition no oil starvation of the bearing section will occur in the event of leakage of the inside air from the stator.

Consequently, the air motor is best suited for use for high-speed rotation, going a long way towards an improvement in durability.

6. Since the backward turn of the grip is restricted by a distance until hitting of the grip against the split ring, the user (including an unskilled user) is confused into thinking that the larger the amount of backward travel, the larger the valve opening, and if he turns the grip excessively, the grip will not drop off. That is, the device is easy to use.

These and other objects, features and advantages of the present invention will become more apparent upon a reading of the following description and accompanying drawings.

DETAILED DESCRIPTION OF THE PREFERRED EMBODIMENT

Next, preferred embodiments of the air motor according to the present invention will be explained with reference to the accompanying drawings.

Figure 10:
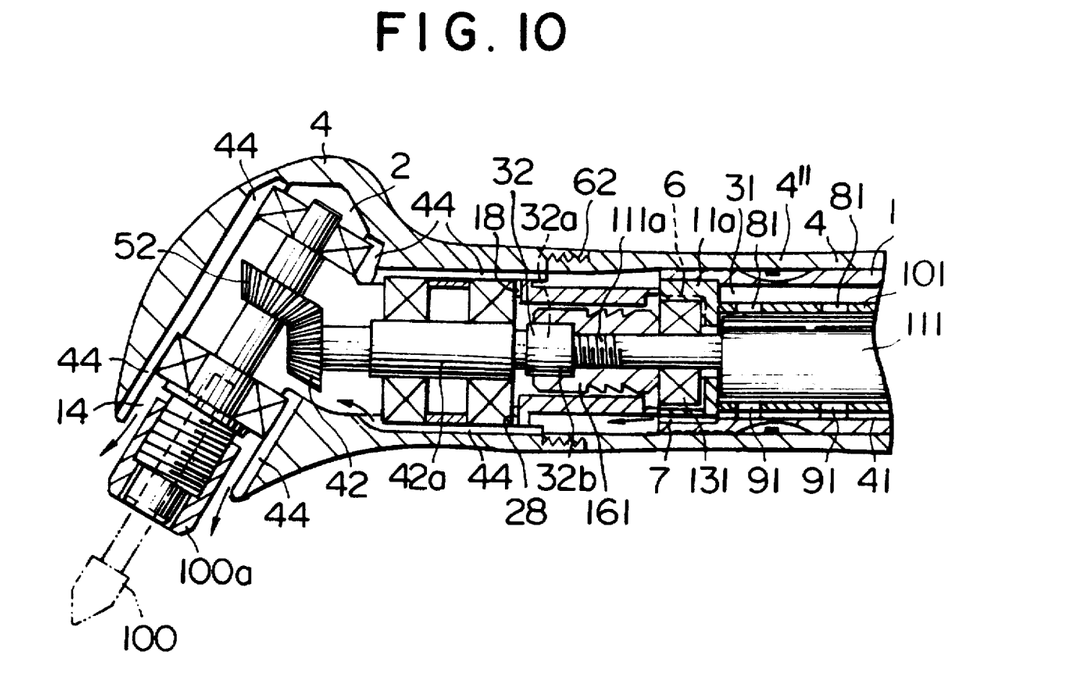
FIG. 10 is a longitudinal sectional view of a second embodiment with an intermediate section omitted.
Figure 11:
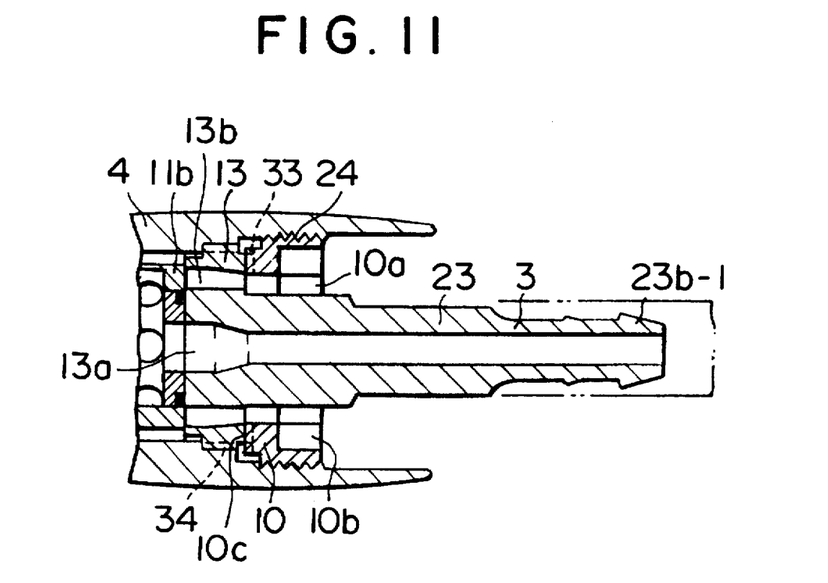
FIG. 11 is a longitudinal sectional view of a major portion of a third embodiment.

FIGS. 1 to 9 show an air motor of the first embodiment; FIG. 10 shows an air motor of the second embodiment; and FIG. 11 gives an air motor of the third embodiment. First, the first embodiment will be explained.

Figure 1:
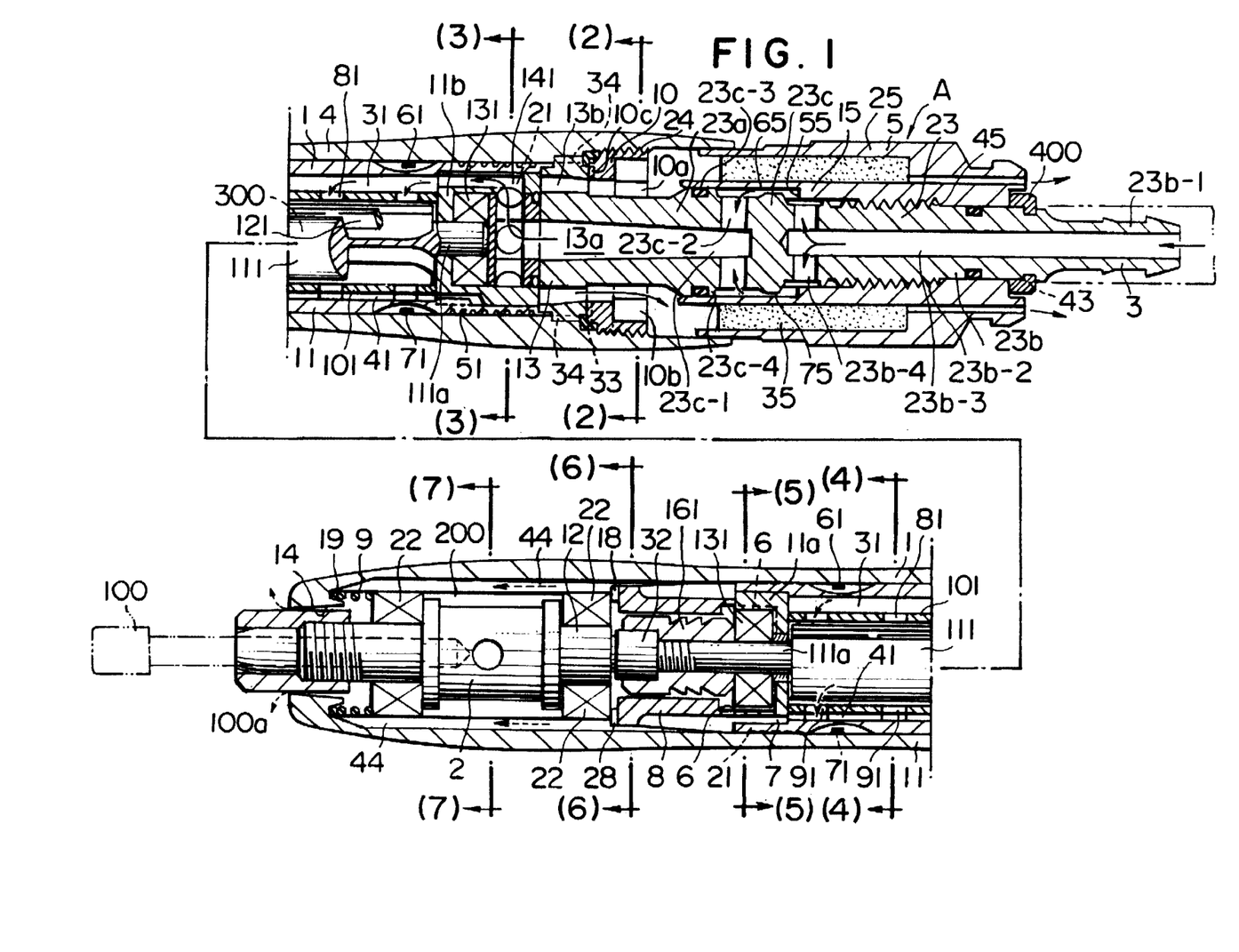
FIG. 1 is a longitudinal sectional view of a first embodiment with an intermediate section omitted.
Figure 2:
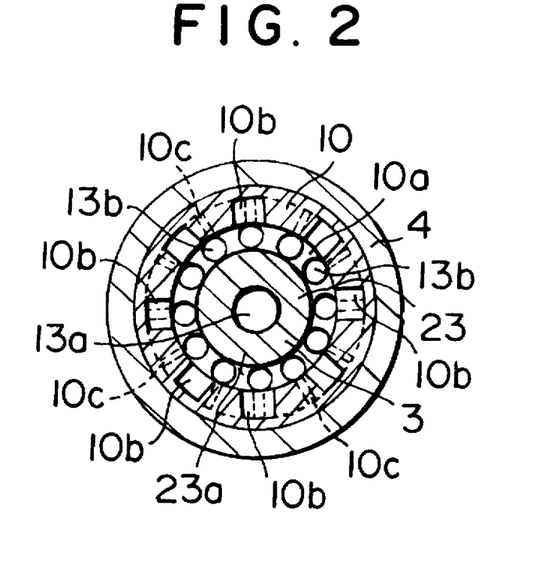
FIG. 2 is a sectional view taken along line (2)—(2) of FIG. 1.

An air motor A comprises an engine pack 1, a grinding-polishing unit 2, an air supply joint 3, a housing 4, and a grip section 5.

Figure 9:
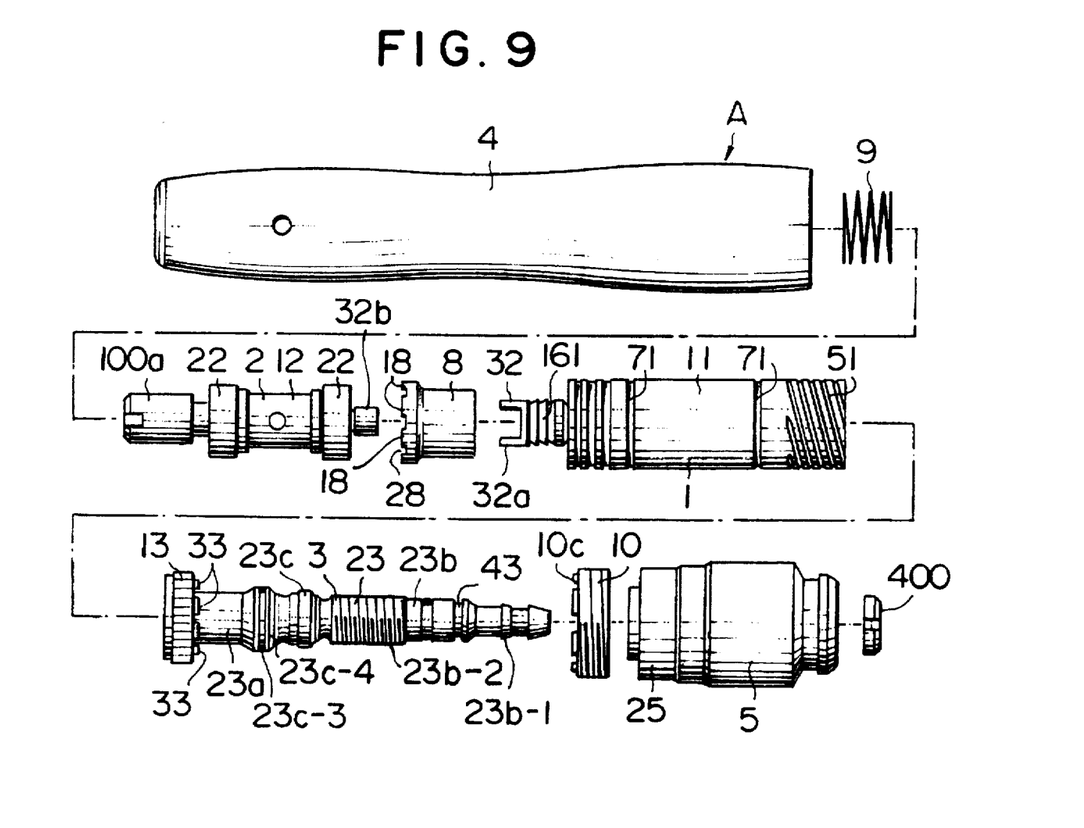
FIG. 9 is an exploded view.

The engine pack 1, as shown in FIG. 1 or 9, is provided with recessed mounting ports 21, 21, for mounting a front retainer 11a and a rear retainer 11b, at the front and rear opening ends of a pipe-like case 11; in the peripheral wall section between the mounting ports 21, 21 are formed an air supply passage 31, an air discharge passage 41 at a spacing along the axial center; in the vicinity of both ends of the outer peripheral surface are formed spiral grooves 51; and a couple of grooves 71 for fitting an elastic annular member 61 are provided at a spacing, in the outer peripheral surface section between the spiral grooves 51.

Figure 4:
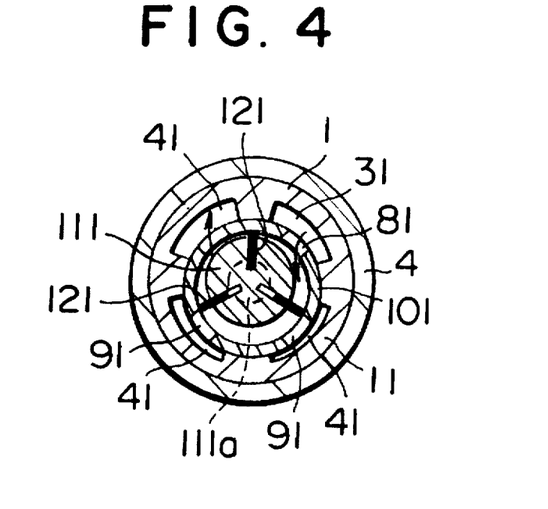
FIG. 4 is a sectional view taken along line (4)—(4) of FIG. 1.

In this engine pack 1, as shown in FIGS. 1 and 4, the front retainer 11a and the rear retainer 11b are fixedly fitted in the mounting ports 21, 21; between the front and rear retainers 11a and 11b a tubular stator 101 having an air supply port 81 exposed to the air supply passage 31 and an air discharge port 91 exposed to the air discharge passage 41 either of which is open in a porous form. In the stator 101 a rotor having a plurality of foldable vanes 121 is mounted with a rotor shaft 111a supported on bearings 131, 131 which are supported by the front retainer 11a and the rear retainer 11b, offset with respect to the axis of the stator 101. The engine pack 1 is unitized with a labyrinth 161 attached on the forward end of the rotor shaft 11a.

Figure 5:
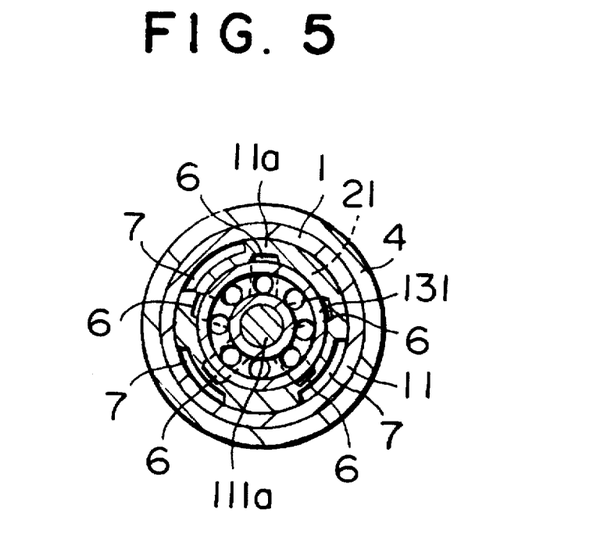
FIG. 5 is a sectional view taken along line (5)—(5) of FIG. 1.

The front retainer 11a, as shown in FIG. 5, is provided with an escape groove 6 for leading the high-pressure inside air in the stator 101 out to the engagement section where the front retainer 11a is engaged with the bearing section 131; and in the peripheral wall section is open a discharge passage 7 which communicates with the air discharge passage 41 for discharging a part of the discharge air.

Figure 3:
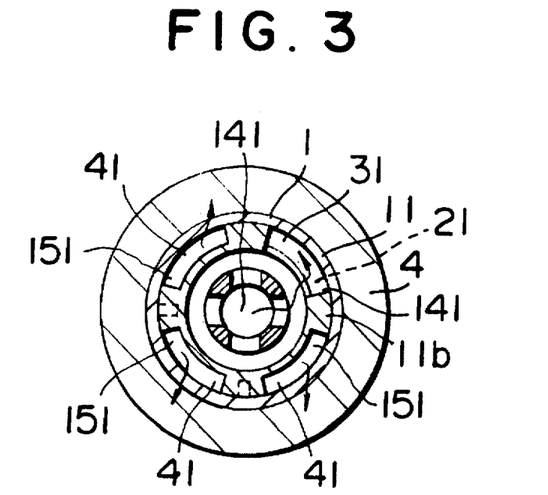
FIG. 3 is a sectional view taken along line (3)—(3) of FIG. 1.

The rear retainer 11b is provided with a communicating air supply passage 141 communicating with the air supply passage 31 in the peripheral wall section, and a communicating air discharge passage 151 as shown in FIGS. 1 and 3. The communicating air supply passage 141 communicates with the air supply joint 3 described later, while the communicating air discharge passage 151 is left open.

The communicating air supply passage 141 and the communicating air discharge passage 151 are separated from each other; the supply air is fed through the air supply joint 3, while the discharge air is exhausted through the communicating air discharge passage 151.

The grinding-polishing tool unit 2, briefly, has, on the forward end, a collet section 100a which allows replacement of the grinding-polishing tool 100 to a desired grinding-polishing tool, and supports a rotating shaft 12 on a pair of front and rear bearings 22. To the rear end of the rotating shaft 12, an engaging-disengaging means 32 is mounted for straightly releasably connected to the rotor shaft 111a of the engine pack 1.

Figure 6:
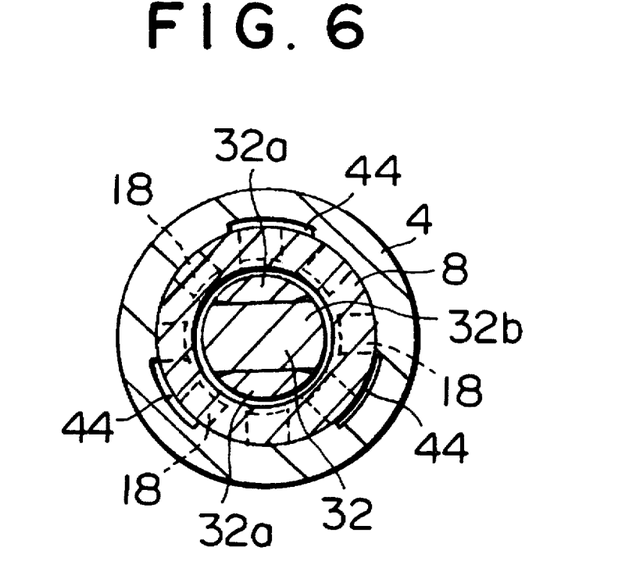
FIG. 6 is a sectional view taken along line (6)—(6) of FIG. 1.

The engaging-disengaging means 32 is a coupling for straightly releasably connect the front end of the rotor shaft 111a, or particularly the labyrinth 161, to the rear end of the rotating shaft 12 of the grinding-polishing tool unit 1 as shown in FIGS. 1 and 6, and is capable of transmitting the rotation of the rotor to the rotating shaft 12 of the grinding-polishing tool unit 2 simply by straightly engaging the rotor shaft 11a with the rotating shaft 12, which can easily be disengaged by drawing; and furthermore the engine pack 1 and the grinding-polishing tool unit 2 can be separated.

To give a further detailed description, either one of the labyrinth 151 and the rotating shaft 12 is provided with a bifurcated connecting piece 32a, 32a projecting at a spacing in the axial direction, and the other is provided with an engaging shaft portion 32b to be inserted into the connecting piece 32a, 32a, so that the connecting piece 32a, 32a may be straightly engaged with, and disengaged from, the engaging shaft portion 32b.

A reference numeral 8 denotes a riser pipe interposed between an outer ring of the front bearing section 131 of the engine pack 1 and an outer ring of the rear bearing section 22 of the grinding-polishing tool unit. Projections 18 are formed at an appropriate spacing on a pipe end which is in contact with the outer ring of the bearing section 22 of the grinding-polishing tool unit 2, forming a passage 28 therebetween.

The housing 4 is a cast molding of a desired synthetic resin, one end of which, or the front open part of which, is narrowed to provide a projection port 14 of the grinding-polishing tool 100, while the other end, or the rear open part, is provided with an internal screw thread 24 on the inner peripheral surface a little inside, and guide projections 34 are formed in the axial direction on the inner peripheral surface ahead of the internal screw thread 24.

Figure 7:
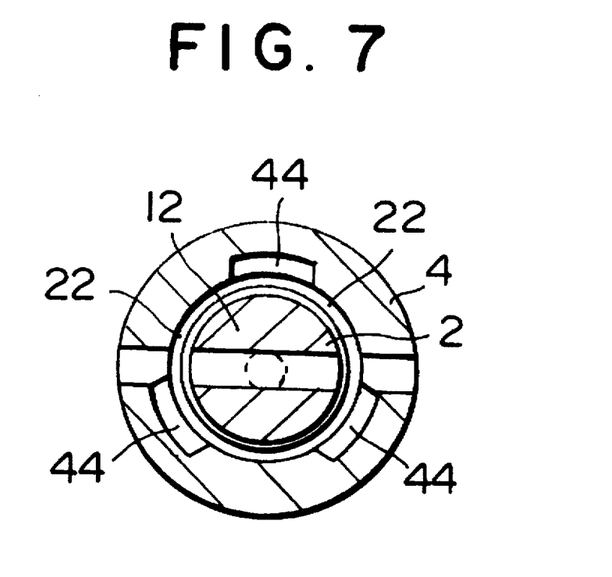
FIG. 7 is a sectional view taken along line (7)—(7) of FIG. 1.
Figure 8:
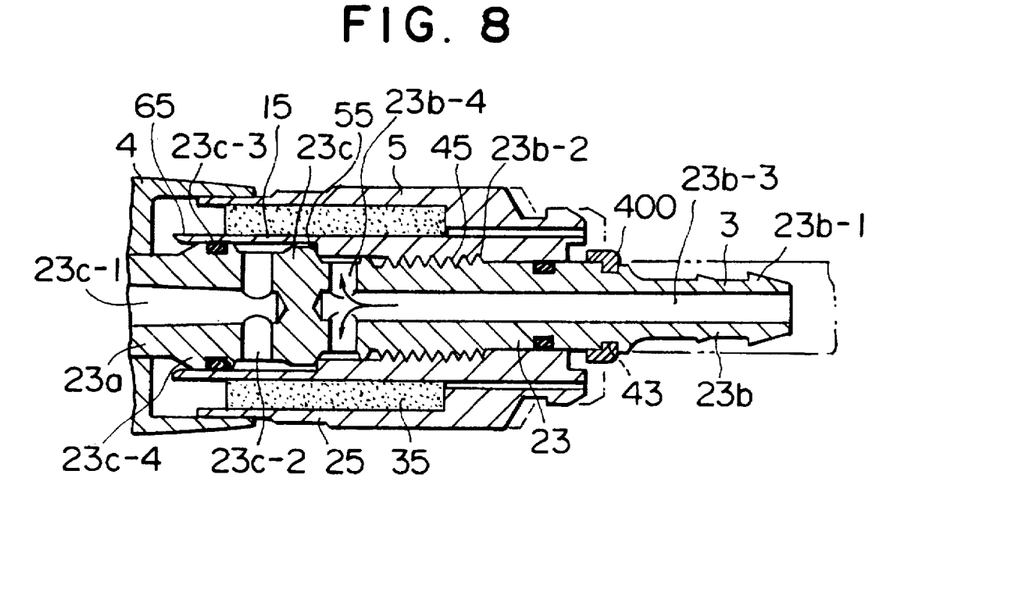
FIG. 8 is an enlarged sectional view of a major portion showing a valve in closed state.

Also the housing 4 is provided with a stepped portion 19 for fitting a spring 9 in the inner peripheral surface in the vicinity of the front opening part; the front half part is a first housing section 200 for accommodating the grinding-polishing tool unit 2, and most of the rear half part is a second housing section 300 for mounting the engine pack 1. In the inner peripheral surface of the first housing section 200 are formed several air discharge grooves 44 which communicate with the discharge passage 7 through an outer space of the riser pipe 8 and are open at the projection port 14 of the grinding-polishing tool 100 (FIG. 7).

Furthermore the engine pack 1 is formed about 2/100 mm smaller in outside diameter than the second housing section 300, and is fitted with an O-ring as an elastic annular member 61 in the O-ring fitting groove 71.

Then, the grinding-polishing tool unit 2 and the engine pack 1 are set by inserting the spring 9, the grinding-polishing tool unit 2, the riser pipe 8, and the engine pack 1 in order of mention into the housing 4. In this state, the grinding-polishing 100 on the forward end protrudes outside at the projection port 14, being straightly engaged and connected with the grinding-polishing tool unit 2 and the engine pack 1 to enable driving power transmission.

The guide projections 34 of the housing 4 are splines, keys, etc. for guiding the air supply joint 3 into contact with the rear retainer 11b mounted on the rear end of the engine pack 1 without rotating.

The air supply joint 3 having a forward end portion 13 which is unrotatably engaged, by the guide projections 34, from the rear open part of the housing 4, into contact with the rear retainer 11b and an air supply tube section 23 connected to the forward end portion 13, is fastened by a nut member 10.

The forward end 13 has an inlet communicating with the air supply tube section 23 and the communicating air supply passage 141 of the rear retainer 11b, and an outlet communicating with the communicating air discharge passage 151 of the rear retainer 11b with its outer end opened, and also is provided with four face plate-like first projections 33 of rigid synthetic resin, which project at an equal spacing on the same circumference, on the outer rear surface of the outlet as shown in FIG. 9. The nut member 10, as shown in FIGS. 1 and 9, has a clearance hole 10a at center which is open for insertion of the air supply tube section 23. Around the clearance hole 10a are provided stepped portions 10b recessed at a spacing for insertion of a jig (not illustrated). On the front surface corresponding to the first projections 33 are provided 12 face plate-like second projections 10c at an equal spacing on the same circumference. The nut member 10, therefore, is tightened by turning the jig (not illustrated) which is engaged with the stepped portion 10b for insertion, elastically deforming the second projections 10c by the first projections 33, and accordingly being firmly secured with the elastic force of restoration of the first projections 33 plus the locking effect of both the second projections 10c and the first projections 33 as well in such a manner that the nut member 10 will not be loosened.

The air supply tube section 23 has an intermediate collar-shaped projection 23c longitudinally lying inside and partly protruding like a collar, by which the air supply tube section 23 is separated into a front tube section 23a and a front tube section 23b which are integrally formed; the rear tube section 23b opens the rear air supply passage 23b-3 which extends to the intermediate collar-shaped projection 23c inside, and has an external screw 23b-2 before a telescope-shaped connecting portion 23b-1 at rear, and a first air supply hole 23b-4 which is open to communicate with the rear air supply passage 23b-3 before the external screw 23b-2; the front tube section 23a opens the front air supply passage 23c-1 communicating with the communicating air supply passage 141 and also has a second air supply hole 23c-2 which is open to communicate with the front air supply passage 23c-1 before the intermediate collar-shaped projection 23c; and ahead of the second air supply hole 23c-2 is located, around the circumference, a front collar-shaped projection 23c-4 which is a little larger in diameter than the intermediate collar-shaped projection 23c and fitted with an O-ring 23c-3.

The grip section 5, as shown in FIG. 1, is of a double construction integrally having an inner tube 15 and an outer tube 25, with the front end inserted into the rear end of the housing 4. Between these two tubes 15 and 25 is mounted a sound-deadening filter 35 and the rear end between these tubes 15 and 25 is opened to discharge the air out at the outlet after deadening its sound. The inner tube 15 has an internal screw 45 corresponding to the external screw 23b-2, a stepped seat face 55 which the rear side face of the intermediate collar-shaped projection 23c contacts, and an expanded tube section 65 which constitutes the forward portion of the stepped seat face 55 with which the front collar-shaped projection 23c-4 slides into contact. The air is supplied to the communicating air supply passage 141 from the first air supply hole 23b-4 through the second air supply hole 23c-2 and a clearance 75 formed between the intermediate collar-shaped projection 23c and the inner peripheral surface of the expanded tube section 65 by turning to withdraw the grip section 5.

Furthermore, if the grip section 5 is further withdrawn after the whole part of the first air supply hole 23b-4 has appeared out to the expanded tube section 65, the valve opening remains unchanged, defying further grip rotation.

In order to prevent this, therefore, there is releasably mounted a split ring 400 in an engaging groove 43 formed in the telescope-shaped connecting portion 23b-1, which is the base end of the air supply joint 2, to thereby stop the backward movement of the grip section 5 when the valve opening has reached a fixed value.

Next, procedures for assembling and disassembling the air motor of the first embodiment will be briefly explained. As shown in FIG. 9, the spring 9, the grinding-polishing tool unit 2, the riser pipe 8, and the engine pack 1 are inserted in order of mention into the rear open section of the housing 4. In this state, the grinding-polishing tool 100 at the forward end protrudes out from the projection port 14, to thereby straightly move the grinding-polishing tool unit 2 into engagement with the engine pack 1 to allow transmission of the driving force.

Next, the nut member 10 is tightened by using a jig (not illustrated) until the forward end of the air supply joint 3 comes in firmly airtight contact with the rear retainer 11b of the engine pack 1.

Subsequently, there is mounted the grip section 5 for adjusting the amount of valve opening by moving an internal screw 45 threadedly into engagement with the external screw 2b-2 of the air supply tube section 23 of the air supply joint 3, thus engaging the split ring 400 with the engaging groove 43 of the connecting portion 23b-1.

In this state, when the grip section 5 is moved backward by a specific amount, the valve is opened, allowing the supply of the compressed air to the air supply passage 31 through the communicating air supply passage 141. The air, then, jets out at the air supply port 81 against the vanes 121 in the stator 101, thus driving the rotor 11 to turn the grinding-polishing tool 100 at a high speed.

The air flows to the sound-deadening filter 35 through the air discharge passage 41 and the communicating air discharge passage 151, being discharged out at the rear end of the grip section 5.

In the meantime, when the air motor is to be disassembled for repair and inspection, the split ring 400 is removed and the grip section 5 is moved back and removed. Then, a jig (not illustrated) is inserted into the stepped portion 10b for insertion to turn to disengage the nut member 10 with force. Thus the air supply joint 3, the engine pack 1, and the grinding-polishing tool unit 2 can be removed in order of mention from the rear open section of the housing 4.

As described above, even an unskilled person can easily assemble and disassemble the air motor without relying upon a special skilled engineer.

Furthermore, the air motor has the following advantages. Since the elastic annular member 61 is mounted on the outer peripheral surface of the engine pack 1 for absorption of vibration during operation, the housing 4 gives a good feel of grip. A high-pressure air leaking from the stator 101 during operation is discharged from the passage 28 through inside the riser pipe 8 and also from the projection port 14 of the grinding-polishing tool 2 through several discharge grooves 44 formed in the inner peripheral surface of the housing section of the grinding-polishing tool unit 2; and a part of the discharge air is discharged from the outside space of the riser pipe 8 through the air discharge groove 44. And therefore if the air in the stator 101 leaks, the air motor will not be subjected to oil starvation. In addition, the bearing section liable to overheat during high-speed operation of the grinding-polishing tool unit 2 can be cooled effectively. Accordingly there will never occur such an accident that the grip section 5 will fall. The air compressed when the engine pack is set can be discharged out through the spiral groove 51, and the engine pack 1 can exactly be engaged with the grinding-polishing tool unit 2.

Next, to explain the second embodiment, the second embodiment is a modification of the aforesaid angle-type grinding-polishing tool unit 2, in which a special housing is integrally provided as a half body of housing 4', which is of the same constitution as the first embodiment except for the design that the special housing can be removably assembled and disassembled through screw threads in relation to the housing body 4" for housing the engine pack 1. It should be noted that common members are designated by the same reference numerals and are not described.

The grinding-polishing tool unit 2 of the second embodiment is, briefly speaking, of the angle type as shown in FIG. 10; a first pinion 42 having one of the engaging-disengaging means 32 at the rear end of the half body of the housing 4' which is open at both ends is rotatably supported on bearings; and at the same time a second pinion 52 for changing the rotation of the first pinion 42 to rotation in a rectangular direction is supported on bearings. On the forward end of the second pinion 52 the grinding-polishing tool 100 is replaceably mounted.

In a desired place on the inner peripheral surface of the half body of housing 4' of the grinding-polishing tool unit 2, several air discharge grooves 44 are formed to discharge the air at the projection port 14 of the grinding-polishing tool 100 similarly to the first embodiment; between the outer peripheral surface of the rear end and the forward end portion of the housing body 4" is located a threadedly engaging portion 62 for engagement of these members, so that one of the engaging-disengaging means 32 formed on the rotating shaft 42a of the first pinion 42 will engage the other one of the engaging-disengaging means 32 formed on the labyrinth 161 of the engine pack 1 at the time of connection through screw threads; and furthermore a part of discharge air from the discharge passage 7 and the leakage air in the stator 10q are discharged from the projection port 14 of the grinding-polishing tool 100 through the air discharge groove 44 similarly to the first embodiment. To describe in detail, connection by screw threads can also ensure discharge of a part of discharge air from the air discharge passage 7 and leakage air from the stator 101 from the projection port 14 of the grinding-polishing tool 100 through the air exhaust groove 44, and through an outside space of the riser pipe 8 and an annular groove 72 formed in the inner peripheral surface which communicates with the air exhaust groove 44 and opens to the housing body 4, in the rear end of the half body of housing 4', so that the passage 28 between the projections 18 on the forward end of the riser pipe 8 will communicate with the air discharge groove 44 of the half body of housing 4'.

The second embodiment makes no difference from the first embodiment in the respect of function and effect, but differs in the feasibility of mounting the separable angle-type grinding-polishing tool unit 2.

The third embodiment is a modification of the air supply joint 4 having no means for adjusting the valve opening, and adopted in place of the air supply joint 3 of the first and second embodiments.

The air motor A is used not only for adjusting the amount of valve opening in the grip section 5 but for a dental handpiece for adjusting the amount of compressed air supply by a foot pedal (not illustrated). In this case, the air supply joint 3, as illustrated, is composed only of the forward end portion 13 and the air supply tube portion 23 having the telescope-type connecting portion 23b-1 in the base end which is the rear end connected to the forward end portion 13. The first air supply hole and the second air supply hole elaborated in the first embodiment are not provided and the grip section is not used as a matter of course.

It is to be noticed that, though not illustrated in the present embodiment, the type of the grinding-polishing tool unit is not limited to the type illustrated and may be of such a type having one of the engaging-disengaging means 32 at the rear end of the rotating shaft.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope and spirit of the invention as defined by the appended claims.

What is claimed is:

1. An air motor having a cartridge-type engine pack which is composed of an air supply passage and an air discharge passage formed of longitudinal grooves in the inner peripheral surface of a pipe-like case which closes a front open section and a rear open section respectively with a front retainer and a rear retainer each having a bearing section, a stator with an air supply port communicating with said air supply passage and an air discharge port communicating with said air discharge passage between said front and rear retainers to open each of a communicating air supply passage and a communicating air discharge passage which communicate with said air supply passage and said air discharge passage respectively, and a rotor having a plurality of vanes and rotatably supported within said stator by said bearing section of said front and rear retainers, said air motor comprising: said engine pack, a grinding-polishing tool unit straightly releasably connecting a rotating shaft to a rotor shaft projecting from said engine pack, a straightly removable air supply joint communicating with said communicating air supply passage of said rear retainer, and a housing which contains said grinding-polishing tool and said engine pack longitudinally releasably inserted in order of mention in a fitted state from a rear opening and is opened at both ends in order to allow projection of said grinding-polishing tool out through said front opening; said air supply joint having a forward end portion which slides into unrotatable engagement with guide projections projectively formed on the inner peripheral surface of said housing in such a manner that it will contact said rear retainer, thereby communicating with said communicating air supply passage, an air supply tube section connected with said forward end portion; and a plurality of first projections produced of a rigid synthetic resin, projecting at an appropriate spacing on the same circumference of the rear surface of said forward end portion; a nut member having a center hole into which said air supply tube section is inserted, and movably engaged by screw threads with the inner peripheral surface of said housing; and a plurality of second projections projectively formed at an appropriate spacing for elastically pressing said first projections against the same circumference of the front surface of said nut member.

2. An air motor according to claim 1, wherein said housing is separable into a half body of housing formed integrally with said grinding-polishing tool unit and a housing body for said engine pack; said half body of housing being removably engaged with said housing body.

3. An air motor according to claim 1, wherein said engine pack has a small clearance communicating with the exterior between said outer peripheral surface thereof and the inner peripheral surface of said housing.

4. An air motor according to claim 1, wherein said engine pack is provided with an elastic circular member mounted, in an optional place on the outer peripheral surface thereof, in tight contact with the inner peripheral surface of said housing, for absorbing vibration.

5. An air motor according to claim 1, wherein said front retainer has an air discharge passage for discharging a part of discharge air and an escape groove for allowing the inside air to the engagement section of said front retainer with said bearing section; said air discharge passage and said escape groove being connected with several air discharge grooves formed in the inner peripheral surface of said housing section of said grinding-polishing tool unit; and said air discharge grooves being open to the projection port where said grinding-polishing tool protrudes.

6. An air motor according to claim 1, wherein said air supply joint has an air supply port communicating with a compressed air supply source, a grip section which is threadedly engaged with said air supply joint, for closing said air supply port when moved forward and for adjusting the amount of opening of said air supply port when moved backward, and a split ring removably mounted on the base end side of said air supply joint for preventing backward movement of said grip over a specific position.

* * * * *

UNITED STATES PATENT AND TRADEMARK OFFICE
CERTIFICATE OF CORRECTION

PATENT NO. : 5,525,097
DATED : June 11, 1996
INVENTOR(S) : Masakazu KAKIMOTO

It is certified that error appears in the above-indentified patent and that said Letters Patent is hereby corrected as shown below:

At column 1, line 35, change "further" to ---further,---.
At column 1, line 45, change "though little despite of an" to ---a little despite the---.
At column 1, line 52, change "will be likely to" to ---will likely---.
At column 1, lines 58 and 59, change "a special knowledge concerned." to ---the concerned special knowledge.---.
At column 2, lines 12 and 13, change "section respectively" to ---section, respectively,---.
At column 2, line 20, change "passage" (second occurrence) to ---passage,---.
At column 2, line 34, change "unrotatable" to ---non-rotatable---.
At column 2, line 50, before "second" insert ---a---.
At column 2, line 54, before "housing" insert ---the---.
At column 2, line 56, before "third" insert ---a---.
At column 2, line 60, before "fourth" insert ---a---.
At column 2, line 66, before "fifth" insert ---a---.
At column 3, line 9, before "sixth" insert ---a---.
At column 3, line 24, change "written" to ---above-described---.
At column 9, lines 12 and 13, change "air, then," to ---air then---.
At column 9, line 47, change "Accordingly" to ---Accordingly,---.

UNITED STATES PATENT AND TRADEMARK OFFICE
CERTIFICATE OF CORRECTION

PATENT NO. : 5,525,097
DATED : June 11, 1996
INVENTOR(S) : Masakazu KAKIMOTO

It is certified that error appears in the above-indentified patent and that said Letters Patent is hereby corrected as shown below:

At column 11, line 5 (claim 1, line 5), change "section respectively" to ---section, respectively,---.
At column 11, line 13 (claim 1, line 13), change "passage" to ---passage,---.
At column 11, line 26 (claim 1, line 26), change "unrotatable" to ---non-rotatable---.
At column 12, line 5 (claim 2, line 2), after "of" insert ---a---.
At column 12, line 7 (claim 2, line 4 ), after "of" insert ---the---.

Signed and Sealed this

Twenty-fifth Day of March, 1997

Attest:

BRUCE LEHMAN

*Attesting Officer*   *Commissioner of Patents and Trademarks*